United States Patent [19]

Tada et al.

[11] Patent Number: 4,731,459
[45] Date of Patent: Mar. 15, 1988

[54] NOVEL ANTI-ULCER AGENTS AND QUASSINOIDS

[75] Inventors: Haruhiko Tada; Masami Doteuchi, both of Osaka; Fumio Yasuda, Hyogo; Koichi Otani, Osaka, all of Japan

[73] Assignee: Shionogi & Co., Ltd., Osaka, Japan

[21] Appl. No.: 866,961

[22] Filed: May 27, 1986

[30] Foreign Application Priority Data

Jun. 14, 1985 [JP] Japan .................................. 60-130516

[51] Int. Cl.[4] .......................................... C07D 493/08
[52] U.S. Cl. .................................................. 549/275
[58] Field of Search ........................................ 549/275

[56] References Cited

FOREIGN PATENT DOCUMENTS 0080570 6/1983 European Pat. Off. .

OTHER PUBLICATIONS

Cassady et al., Academic Press 1980, pp. 254–267.
Odjo et al., CA 97:18987q.

*Primary Examiner*—Jane T. Fan
*Attorney, Agent, or Firm*—Wenderoth, Lind & Ponack

[57] ABSTRACT

Highly effective anti-ulcer agents, i.e. Quassinoids of the following formula:

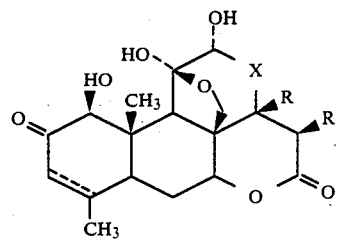

wherein
R is hydrogen or hydroxy;
X is $>C=CH_2$, $>CH-CH_3$, or

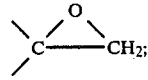

and
the 3,4-dotted line indicates the presence or absence of a double bond.

2 Claims, No Drawings

NOVEL ANTI-ULCER AGENTS AND QUASSINOIDS

BACKGROUND OF THE INVENTION

1. Field of the Invention

The present invention relates to novel anti-ulcer agents chracterized by containing quassinoids as active ingredients and to novel quassinoids as the active ingredients thereof.

2. Prior Arts

Some of quassinoids which have antineoplastic actions have been found from some species of the Simaroubaceae plant. For example, quassin and neoquassin (also called as picrasmin) [Valenta et al., Tetrahedron Letters, 1960, 25; Tetrahedron, 18, 1433 (1962)] have been extracted from *Quassia amara* L. (=*Surinam quassia*) of the Simaroubaceae plant, whose origin is Brazil, Central America; and bruceantin [Kutney et al., Heterocycles, 3, 639 (1975); ibid., 4, 997 (1976); and ibid., 4, 1777 (1976)] from *Brucea antidysenterica* Mill. whose origin is Ethiopia. Further, ailanthone was extracted from *Ailanthus altissima* (Origin: Japan) [H. Naora et al., Chem. Letters, 661 (1982)] and eurycomanone from *Eurycoma longifolia* whose origin is Indonasia [Darise et al., Phytochem., 22, 1514 (1983)]. However, it has never been reported that anti-ulcer actions are recognized on those quassinoids.

Although a patent application disclosing that active ingredients of the Simaroubaceae plant, β-carboline derivatives have an anti-ulcer action has been laied open (JPN Unexam. Pat. Pub. No. 60-58990), they are quite different from the compounds of the present invention in structure.

SUMMARY

Quassinoids which are the active ingredients of the anti-ulcer agents of this invention are shown by the following formula (I):

wherein
R is hydrogen or hydroxy;
X is $>C=CH_2$, $>CH-CH_3$, or and
the 3,4-dotted line indicates the presence or absence of a double bond.

In the formula (I) above, the compound wherein R is hydrogen, X is $=C=CH_2$, and the dotted line indicates the presence of a double bond is known as ailanthone (Ia) which is extracted from *Ailanthus altissima* of the Simaroubaceae plant; and similarly, the compound in which R is hydroxy, X is $=C=CH_2$, and the dotted line indicates the presence of a double bond is known as eurycomanone (Ib) isolated from *Eurycoma longifolia*.

Among the active ingredients of the aforementioned anti-ulcer agents, those except ailanthone (Ia) and eurycomanone (Ib) are novel compounds and can be shown by the following formula (II):

wherein
R and the dotted line each is the same as above, and
Y is $>CH-CH_3$ or provided that the case wherein R is hydrogen, Y is $=CH-CH_3$, and the 3,4-dotted line indicates the presence of a double bond is excluded.

DESCRIPTION OF PREFERRED EMBODIMENTS

Some compounds of a group of quassinoids which have been isolated from Simaroubaceous plants and the study of these compounds focussed on this property have been known to have antineoplastic activities. However, they are far from practical use. The present inventors have prepared ailanthone, eurycomanone and various derivatives of them to examine their biological activities and finally found that those compounds have potent anti-ulcer activities. On the basis of the fact, the present invention provides a new type of agents acting on ulcers.

Typical compounds of the formula (II) are shown below:

13α,18-Epoxy-13,18-dihydroailanthone (IIa),
13β,18-Epoxy-1,3,18-dihydroailanthone (IIb),
3,4,13,18-Tetrahydroailanthone (IIc)
13,18-dihydroailanthone (IId) (in the formula (II), R is hydrogen, Y is $=CH-CH_3$, and the dotted line indicates the presence of a double bond),
13α,18-Epoxy-13,18-dihydroeurycomanone (IIe),
13β,18-Epoxy-13,18-dihydroeurycomanone (IIf),
13,18-Dihydroeurycomanone (IIg), and
3,4-Dihydroeurycomanone (IIh).

These quassinoids (IIa-h) can be prepared from the corresponding starting materials, ailanthone (Ia) and eurycomanone (Ib) by epoxidation and/or reduction of the double bond. For instance, the epoxidation of (Ia) affords the compounds (IIa) and/or (IIb) and the reduction of (Ia) does the compounds (IIc) and/or (IId). Additionally, the epoxidation of (Ib) affords the compounds (IIe) and/or (IIf) and the reduction does the compounds (IIg) and/or (IIh).

The epoxidation of the compound (Ia) or (Ib) may be carried out in a conventional manner for epoxidation of a double bond by using peroxy acids such as performic acid, peracetic acid, trifluoroperacetic acid, perbenzoic acid, m-chloroperbenzoic acid, perphthalic acid, and the like. In case of using m-chloroperbenzoic acid, the reaction may be carried out under cooling or heating or at room temperature in a solvent including ethers such as ethyl ether and tetrahydrofuran; halogenated alkanes such as carbon tetrachloride, chloroform, dichloromethane, and dichloroethane; aromatics such as benzene and toluene; and polar solvents such as acetonitrile and methanol. The epoxy compounds produced in this reaction is generally obtained as a mixture of two isomers but they can easily be separated into the individual isomers by means of chromatography, for example, column chromatography, adsorption-type high performance liquid chromatography (hereinafter referred to as HPLC), reversed phase partition HPLC, thin layer chromatography, and the like.

The reduction of the compound (Ia) or (Ib) may be carried out in a conventional manner for catalytic reduction under hydrogen atmosphere by using, for example, platinum catalysts, palladium catalysts, rhodium catalysts, nickel catalysts, and the like. For instance, a solution of the compound (Ia) in methanol or ethyl acetate is shaken or stirred in the presence of 5% palladium-carbon catalyst under hydrogen atmosphere to give tetrahydro compound (IIc) as a mixture of the epimers. On the other hand, the compound (Ia) is reduced with tris-(triphenylphosphine)rhodium chloride as a catalyst to give the dihydro compound (IId) as a mixture of the epimers. Those epimers can be separated into the individual isomers by chromatography as aforesaid.

The starting materials, i.e. ailanthone (Ia) and eurycomanone (Ib) are isolated by extraction of the aforementioned plants according to the manner shown in the following Preparation. The following Examples illustrate the process for the production of the compounds of the present invention in more detail, the physical constants of the compounds are also shown.

EXAMPLE 1

Epoxidation of Ailanthone (Ia)

To a solution of 112 mg of ailanthone (Ia) in dichloromethane (10 ml) is added m-chloroperbenzoic acid (97 mg, 1.5 equiv.) and the mixture is refluxed for 44 hours while being stirred. The dichloromethane is removed by evaporation in vacuo to leave a residue, which is triturated with ethyl ether to remove soluble substances. The remaining residue is separated by reversed phase chromatography [Develosil®-ODS (Nomura Chemical Co., Ltd.) 15–30 μm; GCH column® (Umetani Precision Co., Ltd.) 20ϕ×250 mm; 30% methanol-water].

By this operation, 11 mg (10%) of the compound (Ia) is recovered and 48 mg (44%) of the α-epoxy compound (IIa) and 35 mg (32%) of the β-epoxy compound (IIb) are obtained as products, whose physical contants are as follows:

(a) α-epoxy compound (IIa):
  mp. 298°–300° C. (dec.).
  $[\alpha]_D$ −52.8° (c, 1.0, pyridine, 23.5° C.).
  IR(KBr): -3440- (br), 1718, 1660, 1621 cm$^{-1}$.
  UV (λ max(95 EtOH)): 240(ε, 11,100) nm.
  MS (SI-MS, m/z): 393 (M$^+$+H).

$^1$H-NMR (pyridine-d$_5$) δ (ppm): 1.59 (s), 1.77 (s), 2.16, 2.06, 2.25, 3.01 (d), 3.07 (d), 3.15, 3.12 (dd), 3.89 (dd), 3.64 (s), 3.94 (s), 3.96 (d), 4.26 (d), 4.51 (s), 4.68, 6.14 (s).
$^{13}$C-NMR (pyridine-d$_5$) δ (ppm): 197.4, 169.5, 162.1, 126.3, 110.2, 84.3, 81.3, 78.3, 71.6, 59.2, 58.0, 45.4, 44.6, 42.4, 31.0, 26.1, 22.4, 10.4.

(b) β-epoxy compound (IIb): Amorphous.
  $[\alpha]_D$−21.6° (c, 1.0, pyridine, 23.5° C.).
  IR (KBr): -3420- (br), 1727, 1673, 1623 cm$^{-1}$.
  UV (λ max(95EtOH)): 240 (ε, 10,200) nm.
  MS (SI-MS, m/z): 393 (M$^+$+H).

$^1$H-NMR (pyridine-d$_5$) δ (ppm): 1.59 (s), 1.76 (s), 2.04, 2.23, 2.06, 2.84 (d), 2.91 (d), 3.01 (dd), 3.71 (dd), 3.12 (d), 3.54, 3.82, 4.23 (d), 4.32 (d), 4.50 (s), 4.69, 6.12 (s).
$^{13}$C-NMR (pyridine-d$_5$) δ (ppm): 197.5, 169.5, 162.3, 126.2, 110.2, 84.3, 81.9, 78.5, 71.4, 59.8, 46.8, 46.7, 46.3, 45.5, 44.9, 42.5, 31.9, 25.9, 22.4, 10.4.

EXAMPLE 2

Catalytic Reduction of Ailanthone (Ia)

(a) To a solution of 32 mg of ailanthone (Ia) dissolved in 4.5 ml of methanol is added 15 mg of 5% Pd-C and the mixture is shaken under hydrogen atmosphere for 4 hours. Additional 10 mg of 5% Pd-C is added thereto and the mixture is shaken for 3 hours. The reaction mixture is filtered to remove the catalyst and then evaporated to give 32 mg of 3,4,13,18-tetrahydroailanthone (IIc) as a mixture of the isomers having different configurations of the methyl group. The mixture of the isomers is subjected directly to the test for biological activities.

$^1$H-NMR (pyridine-d$_5$) δ (ppm): 0.87 (C$_4$-Me), 1.09, 1.34 (C$_{13}$α−, C$_{13}$β-Me), the signal of olefinic proton of the compound (Ia) disappears.
IR (KBr): 3420, 1720, 1635 cm$^{-1}$.

(b) To a solution of 136 mg of anilanthone (Ia) dissolved in 16 ml of methanol is added a solution of 128 mg of tris-(triphenylphosphine)rhodium chloride in 5 ml of methanol, and the mixture is shaken under hydrogen atmosphere for 24 hours. The methanol is removed by evaporation to leave a residue, which is suspended in 30% methanol-water and passed through a silylated silica gel column (64–105 μm, 5 g). The eluate is subjected to reversed phase chromatography [Develosil-ODS (15–30 μm); GCH column 20ϕ×250 mm; 30% methanol-water] to give 66 mg (48%) of the 13,18-dihydro compound (IId) together with 56 mg (41%) of the compound (Ia). The compound (IId), which is a mixture of the isomers having different configurations of the methyl group, is subjected to the test for biological activities.

IR(KBr): 3430, 1725, 1675, 1623 cm$^{-1}$.
$^1$H-NMR (pyridine-d$_5$) δ (ppm): 1.12, 1.36 (C$_{13}$α−, C$_{13}$βMe), 1.75 (C$_4$-Me), 6.11 (C$_3$-H).

EXAMPLE 3

Epoxidation of Eurycomanone (Ib)

To a solution of 101 mg of eurycomanone (Ib) dissolved in 16 ml of acetonitrile is added m-chloroperbenzoic acid (81 mg, 1.5 equiv.) and the mixture is stirred at room temperature for 70 hours. The acetonitrile is removed by evaporation in vacuo to leave a residue, which is triturated with ethyl ether to remove soluble substances. The remaining residue is separated by reversed phase chromatography [Develosil-ODS (15–30 μm); GCH column 20ϕ×250 mm; 30% methanol-water]. In this operation, 24 mg (23%) of the compound (Ib) is recovered and 58 mg (55%) of the α-epoxy compound (IIe) and 18 mg (17%) of the β-epoxy compound (IIf) are obtained as products, whose physical constants are as follows:

(a) α-epoxy compound (IIe):
mp. 260°–261° C.
$[\alpha]_D + 18.2°$ (c, 1.0, pyridine, 23.5° C.).
IR(KBr): 3400, 1735, 1670, 1623 cm$^{-1}$.
UV λ max (95EtOH): 240 (ε, 10,200) nm.
MS (SI-MS, m/z): 425 (M$^+$+H).
$^1$H-NMR (pyridine-d$_5$) δ (ppm): 1.63 (s), 1.79 (s), 2.03, 2.32, 3.27, 2.88 (d), 3.68 (d), 3.80 (s), 4.08 (s), 4.52 (s), 4.09 (d), 4.58 (d), 5.28, 6.06 (s), 6.15 (s).
$^{13}$C-NMR (pyridine-d$_5$) δ (ppm): 197.4, 173.1, 162.6, 126.1, 109.8, 84.5, 81.3, 75.1, 74.1, 72.4, 67.1, 62.7, 52.0, 50.6, 47.4, 45.8, 42.1, 25.6, 22.4, 10.5.

(b) β-epoxy compound (IIf):
mp. >300° C.
$[\alpha]_D + 30.0°$ (c, 0.9, pyridine, 23.5° C.).
IR(KBr): -3440-, 1737, 1666, 1630 cm$^{-1}$.
UV λ max(95EtOH): 240 (ε, 11,000) nm.
MS (SI-MS, m/z): 425 (M$^+$+H).
$^1$H-NMR (pyridine-d$_5$) δ (ppm): 1.63 (s), 1.80 (s), 2.03, 2.34, 3.26 (d), 3.04 (d), 3.80 (d), 3.82 (s), 4.04 (s), 4.07 (d), 4.88 (d), 4.55 (s), 5.19, 5.83 (s), 6.16 (s).
$^{13}$C-NMR (pyridine-d$_5$) δ (ppm): 197.4, 173.8, 162.5, 126.1, 109.6, 84.4, 81.7, 75.6, 75.4, 71.4, 66.9, 59.2, 53.5, 48.4, 46.5, 45.8, 42.2, 25.5, 22.4, 10.4.

EXAMPLE 4

Catalytic Hydrogenation of Eurycomanone (Ib)

To a solution of 69 mg of eurycomanone (Ib) dissolved in 15 ml of methanol is added a solution of 72 mg of tris-(triphenylphosphine)rhodium chloride in 2 ml of methanol, and the mixture is catalytically hydrogenated for 96 hours. The methanol is removed by evaporation to leave a residue, which is then suspended in 30% methanol-water and passed through a silylated silica gel column (64–105 μm, 5 g). The eluate is subjected to reversed phase chromatography [Develosil-ODS (15–30 μm); GCH column 20φ×250 mm; 30% methanol-water] to give 9 mg (13%) of the 13β,18-dihydro compound (IIg-A), 6 mg (9%) of the 13α,18-dihydro compound (IIg-B), and 20 mg (29%) of the 3,4-dihydro compound (IIh), together with 38 mg (55%) of the compound (Ib). The physical constants of the products are as follows:

(a) 13β,18-Dihydro compound (IIg-A):
mp. 257°–258° C. (dec.).
$[\alpha]_D - 12.6°$ (c, 1.0, pyridine, 23.5° C.).
$^1$H-NMR (pyridine-d$_5$) δ (ppm): 1.63 (s), 1.78 (s), 1.86 (d), 2.07, 2.28, 2.86, 3.19 (d), 3.52 (s), 4.15 (d), 4.40 (s), 4.05 (d), 4.65 (s), 5.21, 5.63 (s), 6.12 (s).

(b) 13α,18-Dihydro compound (IIg-B): Amorphous.
$^1$H-NMR (pyridine-d$_5$) δ (ppm): 1.63 (s), 1.68 (d), 1.78 (s), 1.99, 2.27, 3.15 (d), 3.55, 3.64, 4.02 (d), 4.76 (d), 4.29 (s), 4.43 (s), 5.21, 5.45 (s), 6.12 (s).

(c) 3,4-Dihydro compound (IIh): Amorphous.
IR (KBr): 3420, 1720, 1635 cm$^{-1}$.

$^1$H-NMR (pyridine-d$_5$) δ (ppm): 0.92 (d), 1.67 (s), 1.83 (d), -2.3 (m), 2.8- (m), 3.69 (s), 3.99 (d), 4.50 (d), 4.61 (s), 4.78 (s), 5.23, 5.64 (s), 5.62 (d), 6.09 (d).

PREPARATION (1) Isolation of Ailanthone (Ia) from *Ailanthus altissima*

The bark (2 kg) of *Ailanthus altissima* is dipped into chloroform and extracted at room temperature. The organic solvent is removed by evaporation to leave a residue, which is triturated with acetonitrile. The acetonitrile-soluble material is passed through a column of LiChroprep ® RP-18 (made of Merck). The resulting acetonitrile eluate is chromatographed on a silica gel column. Since ailanthone is eluted in 2–5% methanol-dichloromethane fraction, the fraction is refined by a Lobar ® B column (made by Merck) to give a product. This is recrystallized from ethyl acetate to give 1.6 g of ailanthone, mp. 235°–237° C.
$[\alpha]_D + 17.1°$ (c, 1.0, ethanol, 23.5° C.).
$^1$H-NMR (pyridine-d$_5$) δ (ppm): 1.56 (s), 1.76 (s), 2.03, 2.24, 2.86, 2.94, 3.74 (ABX), 3.12 (d), 3.58 (s), 3.66, 4.14 (ABq), 4.49 (s), 4.58 (s), 4.66 (s), 5.20 (d), 5.28 (d), 6.12 (s).
$^{13}$C-NMR (pyridine-d$_5$) δ (ppm): 197.4, 169.7, 162.3, 147.4, 126.2, 118.2, 110.3, 84.3, 80.6, 78.6, 72.2, 47.9, 45.7, 45.5, 44.8, 42.5, 35.3, 26.1, 22.4, 10.2.

(2) Isolation of Eurycomanone from *Eurycoma longifolia*

The root (3 kg) of *E. longifolia* is extracted with 70% methanol-water at room temperature, then evaporated to dryness, and methanol-soluble material is collected. The methanol soluble portion is developed on Sephadex ® G-10 (made by Pharmacia Co.) and the positive fractions by UV detector are collected, then refined by revesed phase chromatography to give a product. This is recrystallized from methanol-ethyl acetate to give 1.0 g of eurycomanone (Ib), mp. 273°–285° C. (dec.)
$[\alpha]_D + 33.7°$ (c, 1.0, pyridine, 23.5° C.).
$[\alpha]_D + 48.6°$ (c, 0.5, ethanol, 23.5° C.).
IR (KBr): 3400 (br), 1735, 1670, 1625 cm$^{-1}$.
MS (SI-MS, m/z): 409 (M$^+$+H).
$^1$H-NMR (pyridine-d$_5$) δ (ppm): 1.63 (s), 1.79 (s), 2.02, 2.34, 3.27 (d), 3.83 (s), 4.03, 4.56 (ABq), 4.53 (s), 4.80 (s), 5.26 (t), 5.66 (s), 5.65 (d), 6.10 (d), 6.16 (br).
$^{13}$C-NMR (pyridine-d$_5$) δ (ppm): 197.5, 173.8, 162.6, 147.8, 126.1, 119.5, 109.7, 84.5, 81.0, 79.4, 75.9, 71.8, 67.7, 52.6, 47.7, 45.9, 42.2, 25.7, 22.4, 10.4.

Effect of the Invention

The following Experiments illustrate the anti-ulcer effect and toxicity data on the compounds of the present invention. The compound numbers in the Experiments correspond to the compound numbers indicated in the Examples above.

EXPERIMENT 1

Effect on ulcer caused by indomethacin

Indomethacin is subcutaneously administered to male SD rats (body weight: 200–220 g) fasted for 24 hours at a dose of 30 mg/kg. The stomachs are excised 7 hours after the administration. The total length of mucosal lesions occurred in the glandular part of the stomach is measured and % inhibition of lesion formation is calculated in comparison with those in the control group. Fifteen minutes before the administration of indomethacin, the test compounds are intraperitoneally administered in a form of aqueous solution. Table 1 shows the results.

TABLE 1

| Compound Nos. | Dose (mg/Kg) | % Inhibition |
| --- | --- | --- |
| Ia | 0.1 | 2.1 |
|  | 0.3 | 44.3 |
|  | 1.0 | 88.7 |
| IIa | 0.3 | 36.8 |
|  | 1.0 | 77.1 |
|  | 3.0 | 100 |
| IIb | 3.0 | 74.4 |
| IIc | 3.0 | 13.7 |
| IId | 3.0 | 67.8 |
| Ib | 0.1 | 12.5 |
|  | 0.3 | 58.5 |
|  | 1.0 | 94.7 |
| IIe | 3.0 | 4.9 |
| IIf | 0.1 | 26.4 |
|  | 0.3 | 71.3 |
|  | 1.0 | 92.6 |
| IIg-A | 3.0 | 47.1 |
| IIg-B | 3.0 | −3.1 |
| IIh | 3.0 | −10.0 |

EXPERIMENT 2

Acute Toxicities

Male ddY mice (Body weight 25–28 g each) are employed for the acute toxicity test. The test compounds are intraperitoneally administered in a form of aqueous solution. Table 2 shows the results.

TABLE 2

| Compound Nos. | LD 50 (mg/Kg) |
| --- | --- |
| Ia | 31.4 |
| IIa | >100 |
| IIb | >30 |
| IIc | >30 |
| IId | >30 |
| Ib | 18.9 |
| IIf | 5.5 |

As clearly understood from the data in Experiments 1 and 2, the compounds of the present invention have remarkable anti-ulcer effects with low toxicities in an effective dosage.

The anti-ulcer agents are very effective in the prophylaxis or treatment of the peptic ulcers such as a gastric or duodenal ulcer. They may be administered orally or parenterally; in case of parenteral use, subcutaneous or intramuscular injection is preferable. As for the formulations, fine granules, granules, capsules, tablets, syrups, solutions, and the like are available for oral use; and solutions or suspensions as injections are for parenteral use. Proper conventional additives may be employed to prepare those formulations. For example, tablets may be prepared by using lactose, sucrose, starch, gelatin, gum arabic, hydroxypropylcellulose, water, and ethanol as carriers, and if necessary, together with conventional disintegrators, lubricants, and the like. The other formulations may be prepared according to the known method.

The anti-ulcer agents contains normally 1–1000 mg, preferably 2–500 mg of the compound (I) in the unit formulation: the contents of the active ingredient may vary with the kind of the formulation. The daily dose of the compound (I) for an adult is 5–1000 mg, preferably 7–500 mg, at which the compound may be administered one or several times a day.

What is claimed is:

1. A compound of the following formula:

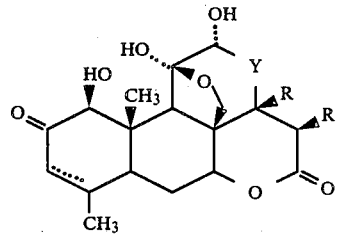

wherein
R is hydrogen or hydroxy;
Y is >CH—CH$_3$ or

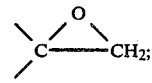

and
the 3,4-dotted line indicates the presence or absence of a double bond provided that the case wherein R is hydrogen, Y is =CH—CH$_3$, and the dotted line indicates the presence of a double bond is excluded.

2. An anti-ulcer composition which comprises an anti-ulcer effective amount of a compound of the formula

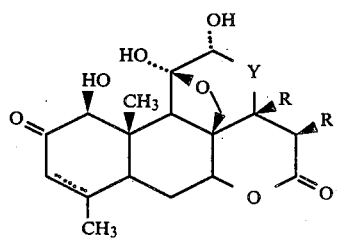

wherein
R is hydrogen or hydroxy;
Y is >CH—CH$_3$ or

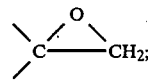

and
the 3,4-dotted line indicates the presence or absence of a double bond provided that the case wherein R is hydrogen, Y is =CH—CH$_3$, and the dotted line indicates the presence of a double bond is excluded, and a pharmaceutically acceptable carrier therefor.

* * * * *